United States Patent [19]

Giannotti et al.

[11] Patent Number: 6,160,179
[45] Date of Patent: Dec. 12, 2000

[54] METHOD OF PRODUCING 4-NITRO-M-PHENYLENEDIAMINE SULFATE

[76] Inventors: James Giannotti; Huayong Song, both of 29-75 Riverside Ave., Middlesex, N.J. 07104

[21] Appl. No.: 09/386,283

[22] Filed: Aug. 31, 1999

Related U.S. Application Data

[63] Continuation-in-part of application No. 09/149,243, Sep. 8, 1998, abandoned.

[51] Int. Cl.[7] .................................................. C07C 209/76
[52] U.S. Cl. .......................................... 564/438; 564/411
[58] Field of Search ...................................... 564/411, 438

[56] References Cited

U.S. PATENT DOCUMENTS 3,639,358   2/1972   Nichols et al. ........................ 528/348

OTHER PUBLICATIONS

Journal Chem Soc., London by Morgan and Wooton vol. 87 part 1 pp. 941, 1905.

CA:104:19407 abs of DE3339922, May 1985.

*Primary Examiner*—Jean F Vollano
*Attorney, Agent, or Firm*—M K Silverman

[57] ABSTRACT

A method of manufacture of 4-nitro-m-phenylenediamine sulfate is taught. The resultant compound is useful in the dyeing of keratinic fibers, particularly, human hair. It exhibits reduced toxicity and potential for damage to such fibers, and is easier to remove than are other known compounds.

4 Claims, No Drawings

METHOD OF PRODUCING 4-NITRO-M-PHENYLENEDIAMINE SULFATE

REFERENCE TO RELATED APPLICATION

This case is a continuation-in-part of Application Ser. No. 09/149,243, filed Sep. 8, 1998, now abandoned.

BACKGROUND OF THE INVENTION

The use of nitro-para phenylenediamine derivatives for use in the dyeing of keratinic (hair) fibers is known in the art as is reflected in U.S. Pat. No. 3,549,303 (1974) and U.S. Pat. No. 3,925,474 (1975), both held by L'Oreal, S. A.

The prior art, as is reflected in the above, as well as in other compositions used in hair coloration, suffer from a common disadvantage, that being damage to many hair types and a permanent character of the hair coloration. This for many consumers is an undesirable aspect of the use of hair dyes. Due to the relatively low molecular weight of prior art keratinic dyes, such compounds are able to penetrate the cuticle of the hair prior art keratinic dyes, such compounds are able to penetrate the cuticle of the hair thereby rendering it difficult to remove without use of harsh and potentially damaging stripping agents. Also, it is believed that hair coloring agents that penetrate the cuticle are inherently harmful to the hair regardless of whether or not the user wishes to remove or change the hair color. Many advantages could be associated with a hair coloring agent having a molecular weight sufficiently high such that a hair dye, incorporating such a high molecular weight agent therein, would not penetrate the keratinic fiber, or at least would not penetrate the fiber to the extent of lower molecular weight agents, thereby producing a true temporary or semi-permanent hair coloring agent, that is, one having increased ease of removal.

Where the instant derivative of 4-nitro-m-phenylenediamine is not used as the sole hair coloring agent, it is believed that it can be advantageously mixed with traditional higher molecular weight dyes to reduce the above set forth disadvantages of the prior art while Imparting to a resultant hair dye substantially all of the advantages and objectives as above set forth herein.

In the prior art, as best known to the within inventors, a usable meta bond within a 4-nitro-m-phenylenediamine (hereinafter "4-NMPD") is not known nor is any combination of 4-NMPD with a sulfate to form the present inventive molecular structure, that is, 4-NMPD sulfate.

As is more fully set forth below, it is the addition of the sulfate radical which provides to the inventive molecule its resultant high molecular weight, that is, a molecular weight in the range of 251 to 349.

SUMMARY OF THE INVENTION

The instant invention constitutes a method of manufacture of a composition useful in the dyeing of keratinic fibers, the composition having a chemical name of 4-NMPD sulfate, an empirical formula of $C_6H_7N_3O_2*H_2SO_4$ and having a structural formula of:

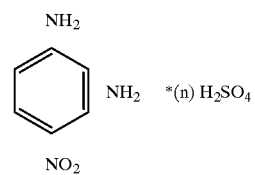

It is an object of the present invention to provide a high molecular weight composition useful in the dyeing of keratinic fibers.

It is another object to provide a composition of the above type usable as a hair colorant for use in temporary and semi-permanent dyes.

It is a further object of the invention to provide a composition of the above type having reduced potential for damage to human hair, the cuticle thereof, or the scalp of a user thereof.

It is a yet further object to provide a composition of the above type which, when applied to the surface of a keratinic fiber, will be substantially removable through the use of washing with an agent furnished with a mild solvent.

It is a still further object of the invention to provide a composition of the above type that is usable with traditional high molecular weight dyes to ameliorate the various disadvantages historically associated therewith.

The above and yet other objects and advantages of the present invention will become apparent from the hereinafter set forth Detailed Description of the Invention and Claims appended herewith.

BRIEF DESCRIPTION OF THE DRAWINGS

There are no drawings in this application.

DETAILED DESCRIPTION OF THE INVENTION

Our process for manufacturing of the inventive composition 4-NMPD sulfate involves a four step reaction beginning with metaphenylenediamine. More particularly, the four step reaction is as follows:

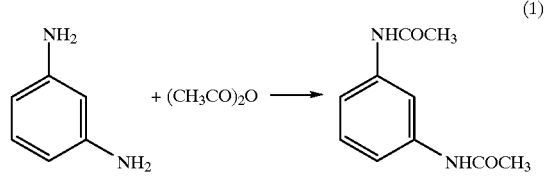

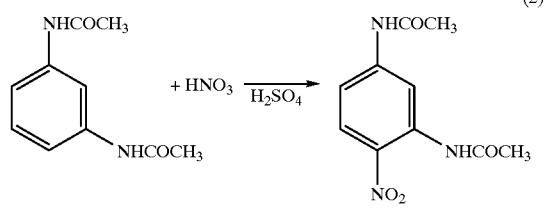

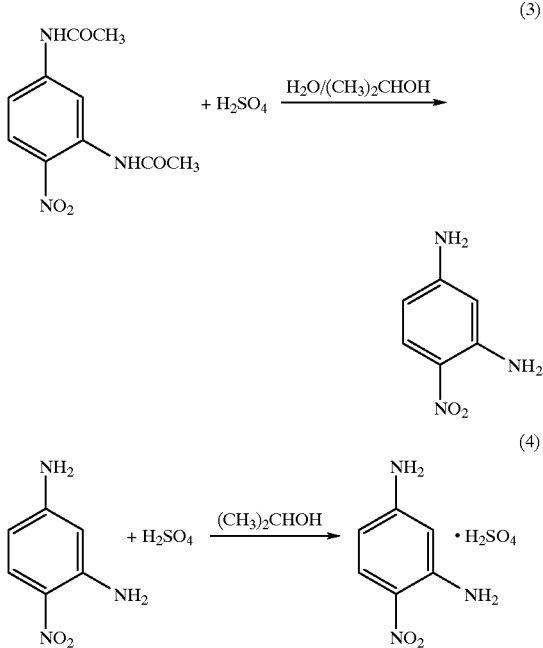

A general process description of the above four step reaction is as follows:

The Initial step of the process involves the reaction between m-phenylenediamine and acetic anhydride. The acetic anhydride should be added slowly since an exothermic reaction will occur Increasing the temperature very rapidly. It is possible to employ acetic acid into the reaction medium to control the temperature as per 2 or more moles relative to m-phenylenediamine. During the addition, maintain the temperature below 80° C. and continue to agitate. Thereafter, water is slowly added to the solution. Continue to agitate for several additional hours from which precipitation will occur. Cool the mixture down below 10–20° C. and filter to recover the precipitate.

The next step involves the addition of nitric acid to the product recovered in the first step, m-diacetanilide. The product recovered in the first step is dissolved in sulfuric acid and the temperature Is maintained below 40° C. After dissolution occurs, the temperature is reduced to below 10° C. where nitric acid is slowly introduced into the reaction. After the addition of nitric acid, continue to agitate and transfer the solution into another vessel containing cold water. Upon precipitation, filter the solid, 4-nitro-m-diacetanilide, for use in the next reaction procedure.

The third step involves the addition of the product recovered in the second step into a solution containing water, sulfuric acid and isopropanol. The mixture is heated for several hours at 85° C. The reaction temperature can vary over a range from 70–90° C. At a temperature below 70° C., a longer reaction time is required and the yields are generally lower. After several hours, the hot solution is filtered to remove water-insoluble impurities. The filtrate Is collected and cooled down to below 40–50° C. The pH of the solution is adjusted to a neutral condition with ammonium hydroxide. After the pH adjustment, the temperature is reduced to below 25° C. with the addition of water. Once again, filter and recover the solid, 4-nitro-m-phenylenediamine.

The last step of the process involves the mixture of 4-nitro-m-phenylenediamine with sulfuric acid in a suitable solvent. The process for the invention is preferably carried out in isopropanol as a solvent. However, water-miscible solvents, such as methanol or ethanol can possibly be used to the aqueous reaction medium. The mixture is heated for several hours at about 75° C. Again, the reaction time varies primarily with the temperature and to a lesser extent with the mole ratio of the reactants. After several hours, the solution is cooled down below 10–20° C., and upon precipitation the product is filtered. The temperature is one of the main contributors to the quality of the product. For example, the addition of sulfuric acid must be maintained below 50° C. and the heating period should not exceed 75° C. If the temperature exceeds these operating conditions the appearance and quality will be affected. In addition, the product is an oxidative dye intermediate; therefore, contact with the air or water will affect the overall quality of the material.

Two methods of preparing the inventive composition according to the invention will now be described, the same purely by way of example. The units of grams (g.) denote parts by weight and percentages (%) denote percentages by weight. The temperatures are given in degrees Centigrade.

EXAMPLE 1

STEP I

In an agitated glass-reaction vessel, 222.0 g. of acetic anhydride is added dropwise to 78 g. of m-phenylenediamine. The temperature is maintained below 50 deg. C. during the addition. After the completion of the acetic anhydride addition, 150 g. of water is added into the solution at a rate of 1 g. per minute. The solution turns off-white to cream upon the addition of water. After 3–4 hours of agitation, a light purple precipitate will form. The precipitate is filtered, washed with cold water and recovered. The recovered wet cake is dried below 80 deg.C. resulting in 100–110 g. of m-diacetanilide. The product will have an off-white appearance with a melting point about 190 deg.C. A 72–80% theoretical yield is obtained relative to m-phenylenediamine.

STEP II

In an agitated glass reaction vessel, 29.0 g. of m-diacetanilide Is added to 143 g. of conc. sulfuric acid. The temperature is maintained below 40 deg. C during the acid addition. Once in solution (approx. 1 hr.) the reaction vessel is placed in an ice water bath to decrease the pot temperature below 10 deg. C. Once at 10 deg. C, 30 g. of 70% nitric acid is added drop-wise to the solution. The temperature is maintained between 10–20 deg. C. After the nitric acid addition, continue to agitate for another 30 minutes. The mixture is then transferred to another vessel containing 500 g. of cold water. After an hour of agitation, the product is filtered. The bright yellow recovered wet cake is dried below 80 deg. C. 32–34 g of 4-nitro-m-diacetanilide is obtained with a melting point about 245 deg.C. A 90–95% theoretical yield is obtained relative to m-diacetanilide.

STEP III

In an agitated glass-reaction vessel, a solution of 60 g. of isopropanol, 120 g. of water, and 40 g of conc. sulfuric acid is heated to 70 deg. At 70 deg. C, 43 g. of 4-nitro-m-diacetanilide is added to the solution. The mixture is heated to 85 deg. C for 4 hours. After 4 hours, the solution is cooled down to 50 deg. C and neutralized to a pH between 6–7 with 27% ammonium hydroxide. After neutralization, agitate for an additional 30 minutes. The mixture is cooled down even further to below 25 deg. C and 150 g. of water is added. After 1 hour, the product is filtered and the recovered wet cake is dried at conditions below 80 deg. C. 23–25 g. of 4-nitro-m-phenylenediamine with a yellow to orange appearance and a melting point above 156 deg.C. A 83 to 90% theoretical yield is obtained relative to 4-nitro-m-diacetanilide.

STEP IV

In an agitated glass-reaction vessel, 50 g. of 4-nitro-m-phenylenediamine is added to 200 g. of isopropanol. While maintaining the temperature below 50 deg. C., 110.0 g. of conc. sulfuric acid is added to the mixture to a pH of 2.0.±0.5. After the acid addition, the mixture is heated to between 70–75 deg. C for 3 hours. After 3 hours, the batch is cooled down to below 30 deg. C. and then agitated for another hour. The product is filtered, washed with water, and dried under conditions below 80 deg. 77–80 g. of 4-nitro-m-phenylenediamine sulfate is obtained resulting in a yellow-brown powder. A 94–97% theoretical yield is obtained relative to 4-nitro-m-phenylenediamine.

EXAMPLE 2

STEPS I–II

The conditions and quantities are identical with those of Example 1, Steps I and II

STEP III

In an agitated glass-reaction vessel, a solution of 60 g. isopropanol, 120 g. of water, and 40 g. of conc. sulfuric acid is heated to 70 deg. C. At 70 deg. C, 43 g. of 4-nitro-m-diacetanilide, prepared to procedures identical with those Example 1, Steps I and II, Is added to the solution. The mixture is heated to 85 deg. C. for 4 hours. After 4 hours, the hot solution is filtered to remove insoluble impurities. The filtrate is cooled down to 50 deg. C. and neutralized to pH between 6–7 with 27% ammonium hydroxide. After neutralization, continue to agitate for an additional 30 minutes. The mixture is cooled down even further to below 25 deg. C and 150 g. of water is added. After 1 hour, the product Is filtered and the recovered wet cake is dried at conditions below 80 deg. C. 22–24 g. of 4-nitro-m-phenylenediamine is recovered with an orange to yellow-brown appearance and a melting point above 156 deg.C. A 79–86% theoretical yield is obtained relative to 4-nitro-m-diacetanilide.

STEP IV

In an agitated glass-reaction vessel, 50 g. of 4-nitro-m-phenylenediamine is added to 200 g. of isopropanol. While maintaining the temperature below 50 deg. C, 110.0 g. of conc. sulfuric acid is added to the mixture. After the acid addition, the mixture is heated between 70–75 deg. C for 3 hours, to a pH of 2.0±0.5. After 3 hours, the batch is cooled down to below 30 deg. C and then agitated for another hour. The product is filtered and dried under conditions below 80 deg. C. 78–81 g. of 4-nitro-m-phenylenediamine sulfate is obtained resulting is a yellow-brown powder. A 95–98% theoretical yield is obtained relative to 4 nitro-m-phenylenediamine.

The formal chemical name of 4-NMPD sulfate is: 4-nitro-meta-phenylenediamine sulfate. Its alternative name is 4-nitro-1, 3-benzenediamine sulfate. Its trade name will be 4-NMPD sulfate. Its empirical formula $C_6H_7N_3O_2*n(H_2SO_4)$ is the same having a molecular weight of 251 where n equals 1, a molecular weight of 300 where n equals 3/2; and a molecular weight of 349 where n equals 2. The resultant structural formula is therefore:

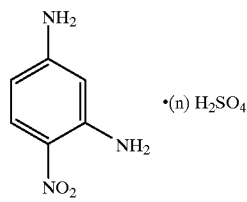

where n may equal 1, 3/2, or 2.

It is to be appreciated that through the addition of a sulfate radical to the 4-NMPD base, the molecular weight is increased by 98. That is, by about 65% over the molecular weight of 4-NMPD alone. This increase in molecular weight is believed sufficient to achieve the objects of the invention as set forth above, that is, to produce a hair colorant agent useful as a temporary or semi-permanent dye and/or agent suitable for mixture with traditional higher molecular weight dyes to thereby ameliorate the disadvantages historically associated with usage thereof.

In tests of the inventive composition, hair coloration accomplished with the inventive composition has resulted in a hair dye which can be removed with a biocompatible solvent, such as ethanol or isopropanol, shampoo such that, after a few washing, the pigment of the hair colorant is no longer perceptible.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

We claim:

1. A method of synthesizing 4-nitro-m-phenylenediamine sulfate comprising the steps of:

(a) diacetylating m-phenylenediamine by adding acetic anhydride to m-phenylenediamine at a temperature below 80° C., thereafter adding water to form an aqueous diacetylating reaction mixture, and agitating said aqueous diacetylating reaction mixture for a sufficient period of time to form diacetyl-m-phenylenediamine precipitate;

(b) nitrating diacetyl-m-phenylenediamine by dissolving diacetyl-m-phenylenediamine formed in step (a) in concentrate sulfuric acid, then reacting nitric acid with dissolved diacetyl-m-phenylenediamine, and forming 4-nitro-diacetyl-m-phenylenediamine precipitate upon adding water into nitrating reaction mixture;

(c) hydrolyzing 4-nitro-diacetyl-m-phenylenediamine formed in step (b) with sulfuric acid in a mixed solvent of water and isopropanol, and forming 4-nitro-m-phenylenediamine precipitate upon neutralizing hydrolysis reaction mixture; and (d) sulfating 4-nitro-m-phenylenediamine by dissolving 4-nitro-m-phenylenediamine formed in step (c) in isopropanol, adding concentrate sulfuric acid at a temperature below 50° C. to adjust pH of sulfating reaction mixture to about 2.0, heating said sulfating reaction mixture to temperatures from about 70° C. to 75° C., and forming 4-nitro-m-phenylenediamine sulfate salt.

2. The method of claim 1, wherein in step (a) said time for agitating said aqueous diacetylating reaction mixture to form diacetyl-m-phenylenediamine precipitate is about three to four hours.

3. The method of claim 1, wherein step (a) further comprises filtering and washing said diacetyl-m-phenylenediamine precipitate with cold water, and drying said diacetyl-m-phenylenediamine precipitate at a temperature below 80° C.

4. The method of claim 1, wherein in step (d) said heating said sulfating reaction mixture is not to exceed 75° C.

* * * * *